United States Patent [19]

Taylor

[11] Patent Number: 4,781,966

[45] Date of Patent: Nov. 1, 1988

[54] SPUNLACED POLYESTER-MELTBLOWN POLYETHERESTER LAMINATE

[75] Inventor: Jack D. Taylor, Roswell, Ga.

[73] Assignee: Kimberly-Clark Corporation, Neenah, Wis.

[21] Appl. No.: 919,273

[22] Filed: Oct. 15, 1986

[51] Int. Cl.⁴ .......................... A47G 9/02; B32B 5/04; B32B 5/26; B32B 27/12; B32B 27/36

[52] U.S. Cl. .................... 428/152; 2/243 A; 5/499; 5/502; 15/209 R; 428/198; 428/200; 428/287; 428/288; 428/296; 428/302; 428/303; 428/339; 428/340; 604/366; 604/370; 604/372

[58] Field of Search ............... 428/152, 198, 200, 287, 428/288, 296, 302, 303, 339, 340

[56] References Cited

U.S. PATENT DOCUMENTS

| | | | |
|---|---|---|---|
| 2,623,031 | 12/1952 | Snyder | 260/45.4 |
| 2,957,512 | 10/1960 | Wade et al. | 154/33.05 |
| 3,016,599 | 1/1962 | Perry | 28/78 |
| 3,594,266 | 7/1971 | Okazaki | 161/173 |
| 3,642,565 | 2/1972 | Ogata et al. | 161/173 |
| 3,673,060 | 6/1972 | Murphy et al. | 161/126 |
| 3,700,545 | 10/1972 | Matsui et al. | 161/175 |
| 3,849,241 | 11/1974 | Butin et al. | 161/169 |
| 3,932,682 | 1/1976 | Loft et al. | 428/296 |
| 3,949,128 | 4/1976 | Ostermeier | 428/152 |
| 4,100,324 | 7/1978 | Anderson et al. | 428/288 |
| 4,150,674 | 4/1979 | Yung | 428/288 |
| 4,234,652 | 11/1980 | Vanomi et al. | 428/296 |
| 4,251,587 | 2/1981 | Mimura et al. | 428/233 |
| 4,296,163 | 10/1981 | Emi et al. | 428/212 |
| 4,318,408 | 3/1982 | Korpman | 128/287 |
| 4,375,446 | 3/1983 | Fujii et al. | 264/518 |
| 4,426,417 | 1/1984 | Meitner et al. | 428/195 |
| 4,426,420 | 1/1984 | Likhyani | 428/224 |
| 4,442,062 | 4/1984 | Fujii et al. | 264/518 |
| 4,555,811 | 12/1985 | Shimalla | 2/51 |
| 4,652,487 | 3/1987 | Morman | 428/913 |
| 4,657,802 | 4/1987 | Morman | 428/913 |
| 4,720,415 | 1/1988 | Weilen | 428/152 |

FOREIGN PATENT DOCUMENTS 1575830 10/1980 United Kingdom .
2132939A 7/1984 United Kingdom .

OTHER PUBLICATIONS

Monsanto Fibers & Intermediates Co. Technical Bulletin MT-3-205-6.

Primary Examiner—James C. Cannon
Attorney, Agent, or Firm—Timothy H. Briggs; Joseph P. Harps

[57] ABSTRACT

A laminate which is elastic in at least one direction, includes an elastic sheet having at least one nonelastic nonwoven web joined thereto at least at two areas. The nonelastic web is gathered between the two areas. The elastic sheet is formed from a polyetherester and the nonelastic nonwoven web includes spunlaced hydraulically entangled polyester fibers. The nonelastic nonwoven web may also include rayon or wood pulp fibers.

24 Claims, 3 Drawing Sheets

SPUNLACED POLYESTER-MELTBLOWN POLYETHERESTER LAMINATE

Field of the Invention

The present invention falls within the field of elastic fabrics, for example, disposable elastic fabrics which may be utilized in the manufacture of wearing apparel and other items which desirably conform about another item.

BACKGROUND OF THE INVENTION

The advent of formation of plastic materials such as plastic sheets, films and nonwoven webs by extrusion processes such as, for example, slot film extrusion, blown bubble film extrusion, meltblowing of nonwoven webs and spinbonding of nonwoven webs allowed a wide variety of products to be manufactured so inexpensively that they could be viewed as disposable after only one or a few uses. Representatives of such products include diapers, tissues, wipes, mattress pads, table cloths and table pads.

Some of the problems in this area are the provision of a bulky elastic material which is resilient and flexible while still having a pleasing feel. A particular problem which has confronted those in the art is the provision of a bulky elastic material which does not feel plastic or rubbery. Other characteristics which are desirable are the ability to withstand unraveling during cutting and sewing operations, good puncture resistance, dyeability, wet strength, the ability to withstand commercial laundering and a low linting factor.

DEFINITIONS

The term "elastic" is used herein to mean any material which, upon application of a biasing force, is stretchable, that is, elongatable, to a stretched, biased length which is at least about 125 percent, that is about one and one quarter, of its relaxed, unbiased length, and which, will recover at least 40 percent of its elongation upon release of the stretching, elongating force. A hypothetical example which would satisfy this definition of an elastic material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, for example, 100 percent or more, and many of these will recover to substantially their original relaxed length, for example, to within 105 percent of their original relaxed length, upon release of the stretching, elongating force.

As used herein, the term "nonelastic" refers to any material which does not fall within the definition of "elastic," above.

As used herein the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein the term "nonwoven web" means a web of material which has been formed without use of weaving processes which produce a structure of individual fibers or threads which are interwoven in an identifiable repeating manner. Nonwoven webs have been, in the past, formed by a variety of processes such as, for example, meltblowing processes, spinbonding processes, film aperturing processes and stable fiber carding processes.

As used herein the term "microfibers" means small diameter fibers having an average diameter not greater than about 100 microns, preferably having a diameter of from about 0.5 microns to about 50 microns, more preferably having an average diameter of from about 4 microns to about 40 microns.

As used herein the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter. Thereafter, the meltblown microfibers are carried by the high velocity gas stream and are deposited on a collecting surface to form a web of randomly disbursed meltblown microfibers. Such a process is disclosed, for example, in U.S. Pat. No. 3,849,241 to Butin and the disclosure of this patent is hereby incorporated by reference.

As used herein the term "sheet" means a layer which may be either a film or a nonwoven web.

As used herein the term "stretch-bonded laminate" refers to a material having at least two layers of nonwoven webs and/or films with at least one of the layers of nonwoven webs and/or films being elastic and at least one of the layers of the nonwoven webs and/or films being nonelastic. The elastic nonwoven web or film layer is joined to the nonelastic nonwoven web or film layer at intermittent joining points or areas while the nonwoven webs and/or films are in juxtaposed configuration and while the elastic nonwoven web or film has a tensioning force applied thereto in order to bring the elastic nonwoven web or film to a stretched condition. Upon removal of the tensioning force after joining of the webs and/or films, the elastic nonwoven web or film will attempt to recover to its unstretched condition and will thereby gather the nonelastic nonwoven web or film between the points or areas of joining of the two layers. The composite material is elastic in the direction of stretching of the elastic layer during joining of the layers and may be stretched until the gathers of the nonelastic nonwoven web or film layer have been removed. A stretch-bonded laminate may include more than two layers. For example, the elastic nonwoven web or film may have a nonelastic nonwoven web or film joined to both of its sides while it is in a stretched condition so that a three layer nonwoven web or film composite is formed having the structure of—gathered nonelastic (nonwoven web or film)/elastic (nonwoven web or film)/gathered nonelastic (nonwoven web or film). Yet other combinations of elastic and nonelastic layers may be utilized.

As used herein the term "palindromic" means a multilayer laminate, for example a stetch-bonded laminate, which is substantially symmetrical. Examples of palindromic laminates would have layer configurations of A/B/A, A/B/B/A, A/A/B/B/A/A, A/B/C/B/A, etc. Examples of non-palindromic layer configurations would include A/B/C, A/B/C/A, A/B/C/D, etc.

As used herein the term "polyetherester" refers to any material having the general formula of:

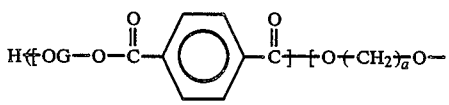

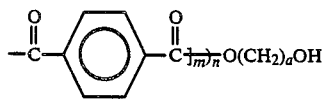

where
"G" is selected from the group including poly(oxyethylene)-alpha,omega-diol poly(oxypropylene)-alpha,omega-diol or poly(oxytetramethylene)-alpha,omega-diol and
"m", "n" and "a" are positive integers. For example, "a" may be 2, 4 or 6.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solid solvents, particulates and materials added to enhance processability of the composition.

OBJECTS OF THE INVENTION

Accordingly, it is an object of the present invention to provide an elastic laminate which is elastic, bulky and has a feel suitable for use in a variety of applications.

Another object of the present invention is to provide an elastic stretch-bonded laminate which is elastic, bulky and has a feel suitable for use in a variety of applications.

Yet another object of the present invention is to provide a bulky laminate including a layer of meltblown polyetherester fibers joined to at least one layer of spunlaced hydraulically entangled polyester fibers.

An even further object of the present invention is to provide a bulky stretch-bonded laminate including a layer of meltblown polyetherester fibers joined to at least one layer of spunlaced hydraulically entangled polyester fibers.

Still further objects and the broad scope of applicability of the present invention will become apparent to those of skill in the art from the details given hereinafter. However, it should be understood that the detailed description of the presently preferred embodiment of the present invention is given herein only by way of illustration because various changes and modifications well within the spirit and scope of the invention will become apparent to those of skill in the art in view of this detailed description.

SUMMARY OF THE INVENTION

In response to the above-discussed problems the present invention provides an elastic laminate which is elastic in at least one direction and which includes an elastic sheet and at least one nonelastic, nonwoven web joined to the elastic sheet at least at two areas, with the nonelastic web being gathered between the two areas.

The elastic sheet is formed from a polyetherester material having the formula:

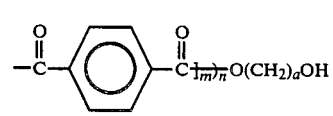

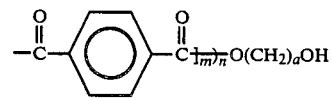

where
"G" is selected from the group including: poly(oxyethylene)-alpha,omega-diol poly(oxypropylene)-alpha,omega-diol poly(oxytetramethylene)-alpha,omega-diol and
"a", "m" and "n" are positive integers. For example, "a" may be 2, 4 or 6.

The polyetherester may have a melt flow rate of from about 5.0 to about 6.0 grams per 10 minutes when measured in accordance with ASTM D-1238 at 190 degrees C. under a 2,160 gram load; a melting point of from about 275 degrees F. to about 350 degrees F. when measured in accordance with ASTM D-3418 (differential scanning calorimeter—peak of endotherm); a specific gravity of from about 1.15 to 1.20 when measured in accordance with ASTM D-792; a tensile stress at break (head speed 2 inches per minute) of from about 2,000 psi to about 4,250 psi when measured in accordance with ASTM D-638; an elongation at break of from about 200 percent to about 600 percent when measured in accordance with ASTM D-638 and a flexural modulus at 212 degrees F. of from about 3,500 psi to about 5,500 psi.

One particular polyetherester has a melt flow rate of about 5.3 grams per 10 minutes when measured in accordance with ASTM D-1238 at 190 degrees C. and under a 2,160 gram load; a melting point of about 298 degrees F. when measured in accordance with ASTM D-3418 (differential scanning calorimeter—peak of endotherm); a specific gravity of about 1.16 when measured in accordance with ASTM D-792; a tensile stress at break (head speed 2 inches per minute) of about 4,050 psi when measured in accordance with ASTM D-638; an elongation at break of about 550 percent when measured in accordance with ASTM D-638 and a flexural modulus at 212 degrees F. of about 3,900 psi.

The elastic sheet is preferably an elastic nonwoven web of meltblown fibers, for example meltblown microfibers. The basis weight of the elastic nonwoven web of meltblown fibers in the relaxed condition may vary from about 10 grams per square meter to about 200 grams per square meter. For example, the basis weight of the elastic nonwoven web may vary from about 20 grams per square meter to about 100 grams per square meter.

The nonelastic web is a nonwoven web of spunlaced hydraulically entangled polyester fibers. The nonelastic web may also include rayon fibers or wood pulp fibers. The nonelastic web has a machine direction sheet grab tensile of from about 10 pounds to about 75 pounds; a cross-machine direction sheet grab tensile of from about 5 pounds to about 50 pounds; a machine direction trapezoid tear of from about 3 pounds to about 40 pounds; a cross-machine direction trapezoid tear of from about 2 pounds to about 45 pounds; a thickness of from about 10 mils to about 45 mils and a basis weight of from about 1 ounce to about 5 ounces per square yard. The nonelastic web may be apertured.

One particular nonelastic web of spunlaced hydraulically entangled polyester fibers has a basis weight of 1.0 ounces per square yard; a thickness of about 11 mils; a machine direction sheet grab tensile of about 17 pounds; a cross machine direction sheet grab tensile of about 8 pounds; a machine direction trapezoid tear of about 7 pounds and a cross machine direction trapezoid tear of about 3 pounds.

One particular apertured nonelastic web of spunlaced hydraulically entangled polyester fibers has a basis weight of about 1.3 ounces per square yard; a thickness of about 18 mils; a machine direction sheet grab tensile of about 25 pounds; a cross-machine direction sheet grab tensile of about 14 pounds; a machine direction trapezoid tear of about 7 pounds and a cross-machine direction trapezoid tear of about 5 pounds.

In one embodiment one of the nonelastic webs of hydraulically entangled spunlaced polyester fibers could be deleted with a nonelastic web of dry laid polyester stable fibers joined by a hot melt polyester-based, powder-form adhesive being substituted therefor. The web of dry laid polyester-based staple fiber may have a basis weight of from about 5 grams per square meter to about 50 grams per square meter, for example about 14 grams per square meter. The polyester stable fibers have a length of from about 1.0 inches to about 2.0 inches, for example about 1.5 inches; a denier of from about 1.0 to about 2.0, for example a denier of about 1.5; a melting point of from about 450 degrees F. to about 500 degrees F., for example about 482 degrees F. and an elongation to break of from about 30 percent to about 50 percent, for example about 40 percent. The hot melt polyester-based adhesive used to hold the polyester staple fibers in a self-supporting web configuration has a density of from about 1.20 g/cm$^3$ to about 1.30 g/cm$^3$, for example about 1.24 g/cm and a melt viscosity of from about 2,000 to 2,200 poise at 190 degrees C., for example a melt viscosity of about 2,100 poise at 190 degrees C. The dry laid web includes from about 78 percent to about 82 percent, by weight, of the polyester staple fibers and from about 18 percent to about 22 percent, by weight, of the hot melt adhesive.

In another embodiment the laminate is a palindromic stretch-bonded laminate which is elastic in at least one direction and which is adapted to stretch at least about 50 percent to about 100 percent, for example, 75 percent in that direction. This preferred laminate includes an inner elastic nonwoven web of meltblown polyetherester fibers hving a relaxed basis weight of from about 20 grams per square meter to about 100 grams per square meter. Also included in this laminate are two outer nonelastic webs of hydraulically entangled spunlaced polyester fibers, each having an ungathered basis weight of from about 0.9 to about 1.1 ounces per square yard; a thickness of from about 10 mils to about 12 mils; a machine direction sheet grab tensile of from about 16 pounds to 18 pounds; a cross-machine direction sheet grab tensile of from about 7 pounds to about 9 pounds; a machine direction trapezoid tear of from about 6 pounds to about 8 pounds and a cross-machine direction trapezoid tear of from about 2 pounds to about 4 pounds.

DETAILED DESCRIPTION OF THE INVENTION

Figure 1:
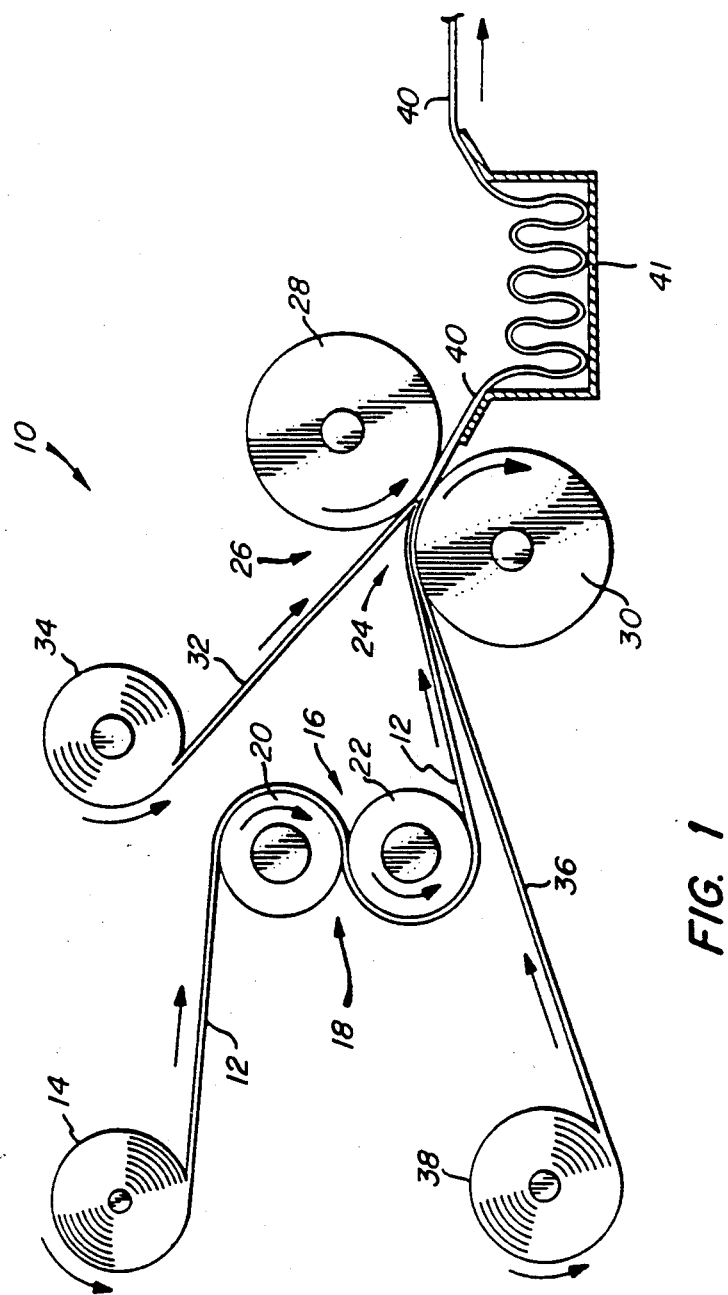
FIG. 1 is a schematic representation of a process for forming a stretch-bonded laminate in accordance with the present invention.

Referring now to the drawings where like reference numbers represent like or equivalent structure and, in particular, to FIG. 1, there is schematically illustrated at 10 a process for forming a stretch-bonded laminate by heat-bonding a nonelastic web to each of the two opposite sides of an elastic sheet which may be an elastic film or an elastic nonwoven web. The elastic sheet 12 is formed from a polyetherester material.

One polyetherester may be obtained under the trade designation Hytrel from the Du Pont Company of Wilmington, Del.

Du Pont literature indicates that at least two grades of Hytrel are available under the trade designations 4056 and G-4078. This literature also reports certain properties of these materials which are summarized below in Table I.

TABLE I

| PROPERTY | Physical Properties of Hytrel (Injection Molded Pieces) | | |
|---|---|---|---|
| | 4056 | G-4078 | ASTM TEST |
| Melt Flow Rate (g/10 min) | 5.3 | 5.4 | D-1238 190° C., 2,160 gram load |
| Melting Point (°F.)* | 298 | 336 | D-3418 |
| Tensile Strength at** Break (psi) | 4,050 | 2,300 | D-638 |
| Elongation at Break (%)** | 550 | 230 | D-638 |
| Flexural Modulus at 212° F. (psi) | 3,900 | 4,900 | D-790 |
| Specific Gravity | 1.16 | 1.18 | D-792 |

*Differential Scanning Calorimeter, peak of endotherm
**Head speed 2 inches/minute From the table, above, it can be seen that these Hytrel polyetherester materials have a melt flow rate of from about 5.0 to about 6.0 grams per 10 minutes when measured in accordance with ASTM D-1238 at 190 degrees C. under a 2,160 gram load; a melting point of from about 275 degrees F. to about 350 degrees F. when measured in accordance with ASTM D-3418 (differential scanning calorimeter—peak of endotherm); a specific gravity of from about 1.15 to 1.20 when measured in accordance with ASTM D-792; a tensile stress at break (head speed 2 inches per minute) of from about 2,000 psi to about 4,250 psi when measured in accordance with ASTM D-638; an elongation at break of from about 200 percent to about 600 percent when measured in accordance with ASTM D-638 and a flexural modulus at 212 degrees F. of from about 3,500 psi to about 5,500 psi when measured in accordance with ASTM D-790.

More particularly, the Hytrel 4056 polyetherester has melt flow rate of about 5.3 grams per 10 minutes when measured in accordance with ASTM D-1238 at 190 degrees C. and under a 2,160 gram load; a melting point of about 298 degrees F. when measured in accordance with ASTM D-3418 (differential scanning calorimeter—peak of endotherm); a specific gravity of about 1.16 when measured in accordance with ASTM D-792; a tensile stress at break (head speed 2 inches per minute) of about 4,050 psi when measured in accordance with ASTM D-638; an elongation at break of about 550 percent when measured in accordance with ASTM D-638 and a flexural modulus at 212 degrees F. of about 3,900 psi when measured in accordance with ASTM D-790.

Another polyetherester may be obtained under the trade designation Arnitel, for example, Arnitel EM-400, from A. Schulman, Inc. of Akron, Ohio.

Schulman literature indicates that at least two grades of Arnitel are available under the trade designations EM 400 and EM 460. This literature also reports certain properties of these materials which are summarized below in Table II.

TABLE II

| PROPERTY | EM-400 | EM-460 | MEASURED BY ASTM STANDARD |
| --- | --- | --- | --- |
| Density | 1.12 | 1.16 | D-792 |
| Melt Point | | | |
| (deg. F.) | 383 | 365 | D-2117 |
| (deg. C.) | 195 | 185 | |
| Water absorption at equilibrium at RT and 50% RH (%) | 0.32 | 0.30 | D-570 |
| Tensile strength (psi) | 2,468 | 3,048 | D-638 |
| Elongation at break (%) | 650 | 700 | D-638 |
| Flexural Modulus (psi) | 7,258 | 14,516 | D-790 |

From the table, above, it can be seen that these Arnitel polyetherester materials have a density of from about 1.10 to about 1.18 when measured in accordance with ASTM D-792; a melt point of from about 350° F. to about 400° F. when measured in accordance with ASTM D-2117; a water absorption at equilibrium, room temperature and 50 percent relative humidity of from about 0.28 percent to about 0.34 percent when measured in accordance with ASTM D-570; a tensile strength of from about 2,250 psi to about 3,250 psi when measured in accordance with ASTM D-638; an elongation at break of from about 600 percent to about 750 percent when measured in accordance with ASTM D-638 and a flexural modulus of from about 6,500 psi to about 15,000 psi when measured in accordance with ASTM D-790.

More particularly, the Arnitel EM-400 polyetherester has a density of about 1.12 when measured in accordance with ASTM D-792; a melt point of about 383° F. when measured in accordance with ASTM D-2117; a water absorption of about 0.32 percent at equilibrium, room temperature and 50 percent relative humidity when measured in accordance with ASTM D-570; a tensile strength of about 2,468 psi when measured in accordance with ASTM D-638, an elongation at break of about 650 percent when measured in accordance with ASTM D-638 and a flexural modulus of about 7,258 psi when measured in accordance with ASTM D-790.

Preferably, the elastic sheet 12 is a web of meltblown polyetherester fibers, for example microfibers, having a basis weight of from about 10 grams per square meter to about 200 grams per square meter. For example, the web may have a basis weight of from about 20 grams per square meter to about 100 grams per square meter.

The elastic sheet 12 may be unwound from a supply roll 14 of the elastic sheet material. The sheet 12 then travels in the direction indicated by the arrows associated therewith and passes through the nip 16 of the S roll arrangement 18 formed by the stacked rollers 20 and 22. Alternatively, the sheet 12 may be formed by known extrusion processes, for example, known film formation or known meltblowing processes, and passed directly through the nip 16 without being first stored on the supply roll 14. The sheet 12 passes through the nip 16 in a reverse-S path as indicated by the rotation direction arrows associated with the stacked rollers 20 and 22. From the S roll arrangement 18 the sheet 12 passes through the pressure nip 24 formed by a bonder roller arrangement 26. The bonder roller arrangement 26 includes a patterned calender embossing roller 28, for example a thermal pin embossing roller, and a smooth anvil roller 30.

A first nonelastic web 32 is unwound from a supply roll 34 and a second nonelastic web 36 is unrolled from a supply roll 38. At least one of the nonelastic nonwoven webs 32 and 36 is a spunlaced web of hydraulically entangled polyester fibers. In one embodiment both of the nonelastic nonwoven webs 32 and 36 are a spunlaced web of hydraulically entangled polyester fibers. One or both of the webs 32 and 36 may also include rayon fibers or wood pulp fibers. The webs 32 and 36 each may have a machine direction sheet grab tensile of from about 10 pounds to about 75 pounds; a cross-machine direction sheet grab tensile of from about 5 pounds to 50 pounds; a machine direction trapezoid tear of from about 3 pounds to about 40 pounds; a cross-machine trapezoid tear of from about 2 pounds to about 45 pounds; a thickness of from about 10 mils to about 45 mils and a basis weight of from about 1 to 5 ounces per square yard. One or both of the webs 32 and 36 may be apertured.

One particular nonelastic web has a basis weight of about 1.0 ounces per square yard; a thickness of about 11 mils; a machine direction sheet grab tensile of about 17 pounds; a cross machine direction sheet grab tensile of about 8 pounds; a machine direction trapezoid tear of about 7 pounds and a cross-machine direction trapezoid tear of about 3 pounds.

One particular apertured nonelastic web has a basis weight of about 1.3 ounces per square yard; a thickness of about 18 mils; a machine grab tensile of about 25 pounds; a cross-machine grab tensile of about 14 pounds; a machine direction trapezoid tear of about 7 pounds and a cross machine direction trapezoid tear of about 5 pounds.

Nonelastic webs of hydraulically entangled fibers of this type can be obtained from Du Pont under the trade designation Sontara, for example, Sontara 8001 and Sontara 8010. Typical physical characteristics of Sontara materials, as evidenced by Du Pont literature are stated below in Table I.

TABLE I

| TYPE | UNIT WEIGHT (oz/yd.$^2$) | THICKNESS (mils) | SHEET GRAB TENSILE (lbs) | | TRAPEZOID TEAR (lbs) | | MULLEN BURST (psi) | FRAZIER AIR PERMEABILITY (CFM/ft$^2$ @ 0.5" H$_2$O) |
|---|---|---|---|---|---|---|---|---|
| | | | MD | XD | MD | XD | | |
| 100% Polyester | | | | | | | | |
| 8000 | 1.2 | 14 | 23 | 14 | 6 | 5 | 40 | 500 |
| 8001 | 1.0 | 11 | 17 | 8 | 7 | 3 | 23 | 600 |
| 8010** | 1.3 | 18 | 25 | 14 | 7 | 5 | 33 | 750 |
| 8100 | 4.0 | 40 | 70 | 45 | 35 | 40 | 120 | 215 |
| 8103 | 2.0 | 22 | 40 | 22 | 14 | 8 | 50 | 290 |
| 8122** | 2.4 | 27 | 45 | 25 | 15 | 7 | 57 | 320 |
| 8125** | 1.8 | 17 | 31 | 16 | 11 | 5 | 44 | 420 |
| 70/30 Rayon/ Polyester Blend | | | | | | | | |
| 8407** | 1.5 | 16 | 11 | 8 | 5 | 7 | 20 | 780 |
| 8423 | 2.3 | 26 | 13 | 15 | 4 | 5 | 24 | 255 |
| 55/45 Woodpulp/ Polyester Blend | | | | | | | | |
| 8801 | 2.0 | 14 | 35 | 17 | 8 | 6 | 35 | 85 |
| 8808 | 2.0 | 14 | 35 | 17 | 8 | 6 | 35 | 85 |
| ASTM Test Method | D1117 Sec. 17 | D1117 Sec. 19 | D1117 Sec. 7 | | D1117 Sec. 14 | | D1117 Sec. 8 | D1117 Sec. 6 |

**Apertured style

Alternatively, one of the nonelastic webs 32 and 36 of hydraulically entangled spunlaced polyester fibers could be deleted with a nonelastic web of dry laid polyester staple fibers joined by a hot melt polyester-based, powder-form adhesive being substituted therefor. The dry laid web is formed by dry laying the polyester staple fibers, adding the polyester-based adhesive in a ground form from above and applying heat to melt the adhesive and join the polyester staple fibers. The web of dry laid polyester-based staple fiber may have a basis weight of from about 5 grams per square meter to about 50 grams per square meter, for example about 14 grams per square meter. The polyester staple fibers have a length of from about 1.0 inches to about 2.0 inches, for example about 1.5 inches; a denier of from about 1.0 to about 2.0, for example a denier of about 1.5; a melting point of from about 450 degrees F. to about 500 degrees F., for example about 482 degrees F. and an elongation to break of from about 30 percent to about 50 percent, for example about 40 percent. The hot melt polyester-based adhesive has a density of from about 1.20 g/cm$^3$ to about 1.30 g/cm$^3$, for example about 1.24 g/cm$^3$ and a melt viscosity of from about 2,000 to 2,200 poise at 190 degrees C., for example a melt viscosity of about 2,100 poise at 190 degrees C. The dry laid web includes from about 78 percent to about 82 percent, by weight, of the polyester staple fibers and from about 18 percent to about 22 percent, by weight, of the hot melt adhesive.

One such dry laid web may be obtained from The Carolina Formed Fabric Corporation of Greenville, S.C. under the trade designation Carelle. Carelle comes in a variety of basis weights and includes from about 78 percent to about 82 percent, by weight, of KODEL 41D polyester stable fibers and from about 18 percent to about 22 percent, by weight, of a polyester-based hot melt adhesive which may be obtained from Eastman under the trade designation FA-300.

The first nonelastic web 32 and the second nonelastic web 36 travel in the directions indicated by the arrows associated respectively therewith as supply rolls 34 and 38 rotate in the directions indicated by the respective arrows associated therewith. both of the nonelastic webs 32 and 36 are directed to pass through the pressure nip 24 of the bonder roller arrangement 26 on the two opposite sides of the elastic sheet 12 as illustrated in FIG. 1. By virtue of the fact that the peripheral linear speed of the rollers 20 and 22 of the S roll arrangement 18 is controlled to be less than the peripheral linear speed of the rollers 28 and 30 of the bonder roll arrangement 26, the sheet 12 is stretched to a selected percent elongation and maintained in such stretched condition during bonding of the nonelastic webs 32 and 36 to the sheet 12 during their passage through the bonder roller arrangement 26. The degree of stretching of the elastic sheet 12 between the S roller arrangment 18 and the bonder roller arrangement 26 may be varied within the elastic limits of the polyetherester sheet 12 to effect different degrees of elongation (elasticity) of the stretch-bonded laminate formed upon bonding of the nonelastic webs 32 and 36 to the elastic sheet 12. In practice it has been found that an elastic stretch-bonded laminate having the ability to stretch at least 50 percent is desirable. For example, an elastic stretch-bonded laminate which is able to stretch from about 50 percent to about 100 percent is desirable. More particularly, an elastic stretch-bonded laminate which is able to stretch about 75 percent is more desirable. In order to form a stretch-bonded laminate having the above degrees of elasticity, it is necessary for the elastic sheet 12 to be stretched to a significantly greater degree upon bonding of the nonelastic webs 32 and 36 thereto. In this regard it has been generally found that the elastic sheet 12 should, upon bonding of the nonelastic webs 32 and 36 thereto, be stretched approximately two times the degree of desired elasticity in the stretch-bonded laminate. Thus, if a stretch-bonded laminate having 100 percent elasticity is desired, the elastic sheet 12 should be stretched about 200 percent at the moment of bonding.

While many bonding methods may be possible, a preferred method of bonding is by thermal bonding and, in particular, by thermal pin embossment where one or both of the patterned embossing calender roller 28 and the smooth anvil roller 30 are heated and the pressure between these two rollers is adjusted by well-known means to provide the desired temperature and bonding pressure to bond the webs 32 and 36 to the sheet 12 and thereby form a composite stretch-bonded elastic laminate 40. In thermal pin embossment bonding, the webs 32 and 36 are bound to the elastic sheet 12 by the action of lands or pins (not shown) which protrude from the calender roller 28 and cooperate with the anvil roller 30 to apply heat and pressure to selected intermittent areas of the three materials 12, 32 and 36 as they pass through the nip 24. This serves to bond them together. A variety of different bonding patterns can be effected in this manner to create a number of different visual effects. Representative bonding patterns are illustrated in FIGS. 3 through 7.

The elastic sheet 12 of the composite elastic laminate 40, upon emergence of the composite elastic laminate 40 from the pressure nip 24 of the bonder roll arrangement 26, is immediately relaxed and quickly recovers and gathers the nonelastic webs 32 and 36 between the intermittent bond areas formed by the bonder roller arrangement 26. Because the direction of stretching of the elastic sheet 12 is generally the same as the direction of travel of the three materials 12, 32 and 36 the generally parallel gathers in the nonelastic webs 32 and 36 will be generally perpendicular to the direction of travel of the composite elastic laminate 40. Thereafter the composite elastic laminate 40 passes to a holding box 41 where it is maintained in a relaxed, unstretched condition for a length of time for the elastic sheet 12 to cool sufficiently to avoid its cooling while it is in a stretched condition and thereby losing all or a considerable proportion of its ability to contract from the stretched dimensions which it has assumed during bonding.

If the composite elastic laminate 40 is to be dyed, the holding box 41 may also serve as an arrangement to apply a liquid dye to the composite elastic laminate 40.

After a brief untensioned period of, for example, up to about 30 seconds, e.g., from about 3 seconds to about 20 seconds, in the holding box 41, the composite elastic laminate 40 is withdrawn therefrom and transferred to a storage roll (not shown). The provision of the holding box 41 or an equivalent structure allows the untensioned heat-bonded composite elastic laminate 40 to stabilize, that is cool, while it is in an untensioned arrangement. This allows the elastic sheet 12 to contrast and gather the gatherable web immediately after bonding of the webs to each other. Additionally, this allows the elastic sheet 12 to cool in a relaxed, that is nontensioned, condition which avoids the elastic web becoming set at the stretched dimensions which it had assumed during bonding. If the elastic sheet 12 were to set in the tensioned state it would be unable to contract and form the generally parallel gathers in the nonelastic webs 32 and 36. Accordingly, the composite material 40 would not possess elasticity because any significant stretching of the composite would result in tearing of the nonelastic webs 32 and 36. In order to avoid loss of part of all of the elasticity of the composite elastic laminate 40, the composite elastic laminate 40 should be transferred to the storage roll in only a slightly tensioned condition. Also, the composite elastic laminate 40 should be stored under only slight tension.

The stretch-bonded laminate can be provided with two directional stretch by stretching the sheet 12 in both the machine direction and cross-machine direction at the moment of bonding of the webs 32 and 36 to the sheet 12. Conventional apparatus for effecting such two direction stretching includes tenter frame arrangements or the use of arched roller systems as is known in the art.

Figure 2:
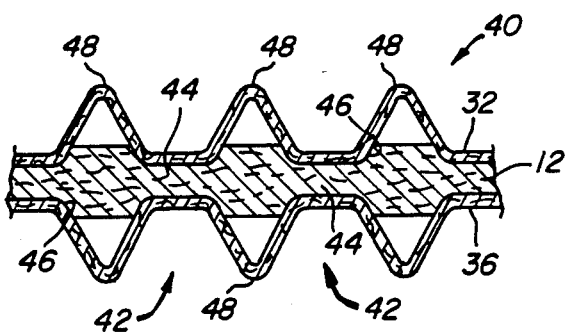
FIG. 2 is a cross-section of a stretch-bonded laminate formed by the process illustrated in FIG. 1 with the laminate being in a relaxed condition to illustrate the gathers.
Figure 3:
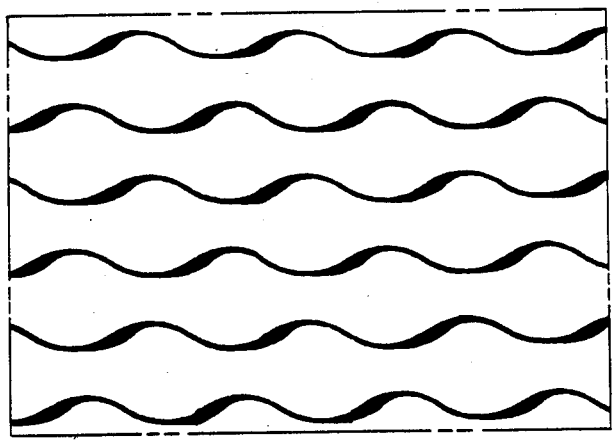
FIG. 3 is a plan view of a stretch-bonded laminate illustrating a bonding pattern.
Figure 4:
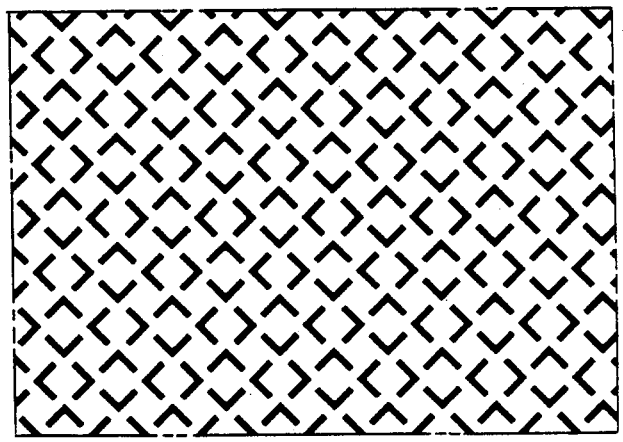
FIG. 4 is a plan view of a stretch-bonded laminate illustrating another bonding pattern.
Figure 5:
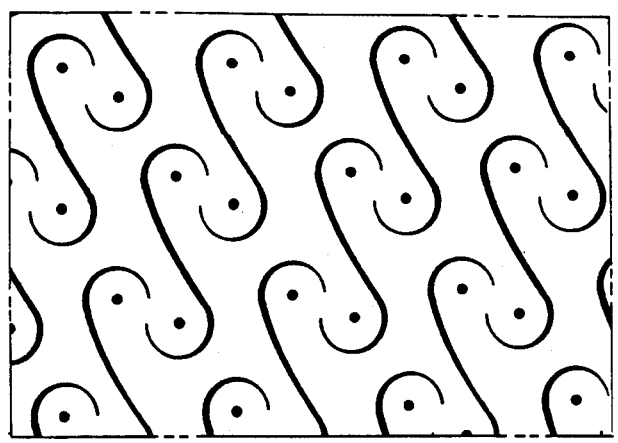
FIG. 5 is a plan view of a stretch-bonded laminate illustrating yet another bonding pattern.
Figure 6:
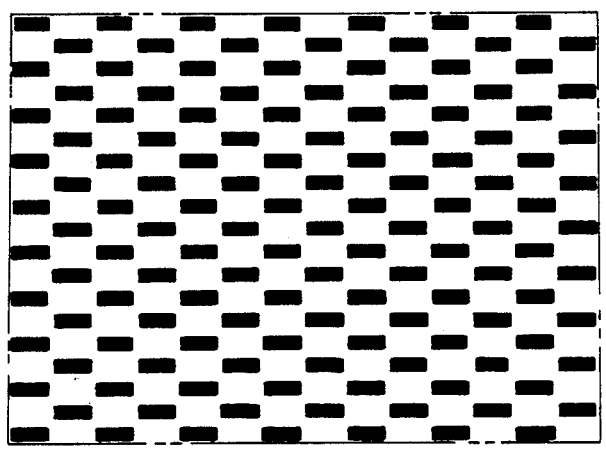
FIG. 6 is a plan view of a stretch-bonded laminate illustrating one other bonding pattern.
Figure 7:
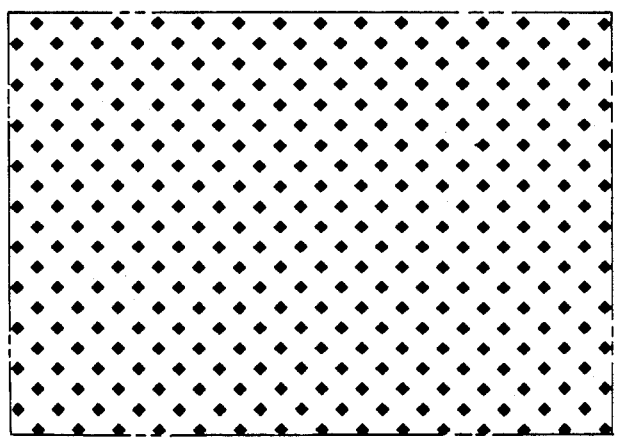
FIG. 7 is a plan view of a stretch-bonded laminate illustrating yet a further bonding pattern.

FIG. 2 which is a cross-sectional view of the elastic composite laminate 40 illustrates that the elastic composite laminate 40 has a plurality of embossed bond sites 42 formed by the action of the raised portions of the embossing calender roller 28 in cooperation with the anvil roller 30. The temperature and pressure maintained in the nip 24 between the calender roller 28 and the anvil roller 30 was such that the pressure and temperature imposed by the raised portions of the calender roller 28 formed indentations 44 within the elastic sheet 12 by softening or melting the portions of the sheet 12. The peripheral portions 46 of the indentations 44 of the sheet 12 include a resolidified portion of the material which was formerly located in the indented area 44. The peripheral portions 46, upon resolidification after their softening or melting in the pressure nip 24 of calender roller 28 and anvil roller 30, tend to form a reasonably strong bond with the overlaid nonelastic webs 32 and 36. The nonelastic webs 32 and 36 are gathered between the bond sites 42 and these gathers are illustrated at 48.

The elastic laminates of the present invention which have outer hydraulically entangled spunlaced nonwoven webs possess a number of desirable characteristics such as, for example, unraveling during cut and sew operations, good puncture resistance, good dyeability, good wet strength and the ability to withstand commercial laundering and low linting. The material is drapeable and has a soft feel as a result of the outer hydraulically entangled surface webs.

EXAMPLES 1-17

The elastic laminates of Examples 1-17 were made in accordance with the present invention by stretch-bonding at least one hydraulically entangled nonwoven web of Sontara obtained from DuPont and selected from those listed in Table I to one side of an elastic web of meltblown fibers formed from a polyetherester. The polyetherester material used to form the elastic web is designated in the column entitled "Elastic Web" of Table III. The material on the calender side of the elastic meltblown is given in the column entitled "Calender Side". The material on the anvil side of the elastic meltblown is given in the column entitled "Anvil Side". The basis weight in grams per square meter of the web of polyetherester meltblown fibers is given in the column entitled "Basis Weight Elastic Web". The temperature in degrees F. of the calender roll is given in the column entitled "Calender Temperature," and the temperature in degrees F. of the anvil roll is given in the column entitled "Anvil Temperature". At the moment of bonding, the web of meltblown polyetherester fibers was stretched approximately the percent given in the column entitled "Percent Stretch at Bonding". The percent stretch in the final elastic laminate, when the gathered layers are fully extended, is given in the column "Percent Stretch in Laminate".

TABLE III

| Example | Calender Side | Anvil Side | Elastic Web | Basis Wt. Elastic Web (gm/m$^2$) | Calender Temperature (°F.) | Anvil Temperature (°F.) | Percent Stretch at Bonding | Percent Stretch in Laminate |
| --- | --- | --- | --- | --- | --- | --- | --- | --- |

TABLE III-continued

| | | | | | | | | |
|---|---|---|---|---|---|---|---|---|
| 1  | S8010  | S8010 | Arnitel EM400   | 80 | 267     | 267     | 173 | N/A   |
| 2  | S8010  | S8010 | Arnitel EM400   | 80 | 292–295 | 289–292 | 173 | 90    |
| 3  | S8010  | S8010 | Arnitel EM400   | 80 | 305     | 310     | 125 | 90    |
| 4  | RD2007 | S8010 | Hytrel 4078     | 80 | 278     | 279     | 141 | 70    |
| 5  | Carelle| S8010 | Arnitel EM400   | 80 | 311     | 310     | 175 | 90    |
| 6  | S8010  | S8010 | Arnitel EM400   | 80 | 307     | 310     | 175 | 80    |
| 7  | S8010  | S8010 | Arnitel EM400   | 50 | 300     | 307     | 175 | 75    |
| 8  | S8010  | S8010 | Arnitel EM400   | 50 | 323     | 325     | 175 | 75    |
| 9  | S8010  | S8010 | Arnitel EM400   | 50 | 339     | 339     | 175 | 70    |
| 10 | S8010  | S8010 | Hytrel 4078     | 80 | 307     | 310     | 175 | 70    |
| 11 | S8001  | S8010 | Arnitel EM400   | 80 | 312     | 320     | 79  | 50    |
| 12 | S8001  | S8010 | Arnitel EM400   | 80 | 334     | 334     | 79  | 55    |
| 13 | S8001  | S8001 | Arnitel EM400   | 50 | 324     | 335     | 113 | 75    |
| 14 | Carelle| S8001 | Hytrel HTX-8037 | 80 | 262     | 263     | 144 | 60    |
| 15 | Carelle| S8001 | Hytrel HTX-8034 | 80 | 288     | 309     | 144 | 60–65 |
| 16 | Carelle| S8001 | Hytrel HTX-8034 | 80 | 307     | 333     | 200 | 80    |
| 17 | Carelle| S8001 | Hytrel HTX-8034 | 50 | 290     | 310     | 167 | 90    |

Comments

Example 1   Virtually no bonding at these conditions. In all examples "S" refers to Sontara.
Example 2   Bonding is fair. The uniformity of the stretch-bonded laminate is good.
Example 3   Bonding and uniformity are good.
Example 4   Bonding is very good. Uniformity is good. Layers are soft. RD2007 is a 37 grams per square yard spunlaced polyester web obtained from Kendall.
Example 5   Bonding is good. The Carelle had a basis weight of 14 grams per square yard.
Example 6   Bonding is fair on both sides with the anvil side being stronger.
Example 7   Bonding is weak to fair. Uniformity is good.
Example 8   Bonding and uniformity are good.
Example 9   Bonding is quite good and uniformity is good. In Examples 7, 8 and 9 bonding improved as the bonding temperature increased.
Example 10  Bonding is excellent. Uniformity is very good.
Example 11  Bonding is fair.
Example 12  Bonding and uniformity are both good.
Example 13  Uniformity and bonding are good.
Example 14  The Carelle had a basis weight of 21 grams per square yard. The Hytrel HTX-8037 is the same as Hytrel 4056 with the exception that Dupont utilized a different stabilizer. Bonding is very good on both sides. The uniformity is very good.
Example 15  Bonding is good on both sides. The Carelle had a basis weight of 21 grams per square yd.
Example 16  Bonding is good. The laminate looks good. The Carelle had a basis weight of 21 grams per square yard.
Example 17  The 90% stretch was surprising. Bonding is good on both sides. Uniformity is very good. There are no pin holes. There is no melt through of the elastic along the bond pattern. The Carelle had a basis weight of 21 grams per square yard.

It is to be understood that the above disclosure of the presently preferred embodiment of the invention is to be taken as illustrative of the invention. Further, it is clear that, in view of the present disclosure, those of skill in the art should be capable of making numerous modifications without departing from the true spirit and scope of the invention. For example, different combinations of nonelastic webs and elastic sheets could be stretch-bonded together. In particular, the elastic laminate of the present invention could include only two layers of material with one of the layers being the sheet of polyetherester material and the other layer being a nonelastic layer of spunlaced polyester.

What is claimed is:

1. A laminate which is elastic in at least one direction, said laminate comprising:
an elastic sheet comprising a polyetherester material having the following formula;

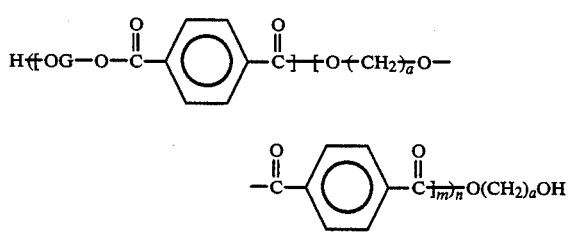

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers; and at least one nonelastic nonwoven web comprising spunlaced hydraulically entangled polyester fibers joined to said elastic sheet at least at two areas, said nonelastic web being gathered between said two areas.

2. The laminate of claim 1, wherein said elastic sheet is an elastic nonwoven web of meltblown fibers.

3. The laminate of claim 2, wherein the basis weight of the elastic nonwoven web is from about 10 grams per square meter to about 200 grams per square meter.

4. The laminate of claim 2, wherein the basis weight of the nonelastic web is from about 1 ounce per square yard to about 5 ounces per square yard.

5. The laminate of claim 2, wherein said polyetherester material has a melt flow of from about 5.0 to about 6.0 grams per 10 minutes when measured in accordance with ASTM D-1238 at 190° C. under a 2,160 gram load.

6. The laminate of claim 2, wherein said meltblown fibers are meltblown microfibers.

7. The laminate of claim 2, wherein the nonelastic web is apertured.

8. The laminate of claim 2, wherein the nonelastic web further comprises fibers selected from the group consisting of rayon fibers or wood pulp fibers.

9. An elastic stretch-bonded laminate adapted to stretch at least about 50 percent in at least one direction, said laminate comprising:

an elastic nonwoven web comprising fibers of a polyetherester material having the formula of;

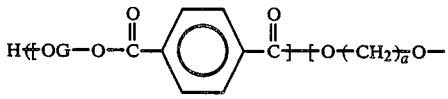

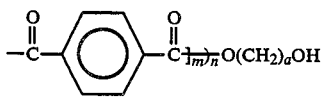

where

"G" is selected from the group including: poly(oxyethylene)alpha,omega-diol poly(oxypropylene)-alpha,omega-diol poly(oxytetramethylene)-alpha,omega-diol and "a", "m" and "n" are positive integers; and at least one nonelastic nonwoven web comprising spunlaced hydraulically entangled polyester fibers joined to said elastic web at least at two areas, said nonelastic web being gathered between said two areas.

10. The stretch-bonded laminate of claim 9, wherein said polyetherester fibers are meltblown fibers.

11. The stretch-bonded laminate of claim 10, wherein the basis weight of the elastic nonwoven web is from about 10 grams per square meter to about 200 grams per square meter.

12. The stretch-bonded laminate of claim 10, wherein the basis weight of the nonelastic web is from about 1 ounce per square yard to about 5 ounces per square yard.

13. The stretch-bonded laminate of claim 10, wherein said polyetherester material has a melt flow of from about 5.0 to about 6.0 grams per 10 minutes when measured in accordance with ASTM D-1238 at 190° C. under a 2,160 gram load.

14. The stretch-bonded laminate of claim 10, wherein said meltblown fibers are meltblown microfibers.

15. The stretch-bonded laminate of claim 10, wherein the nonelastic web is apertured.

16. The stretch-bonded laminate of claim 10, wherein the nonelastic web further comprises fibers selected from the group consisting of rayon fibers or wood pulp fibers.

17. An elastic palindromic stretch-bonded laminate adapted to stretch at least about 50 percent in at least one direction, said laminate comprising:

an inner elastic nonwoven web having a basis weight of from about 20 grams per square meter to about 100 grams per square meter, said elastic web comprising meltblown fibers of a polyetherester material having the formula of:

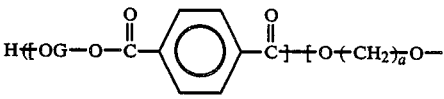

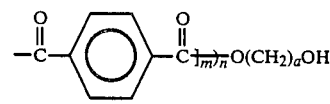

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers; and two outer nonelastic nonwoven webs comprising spunlaced hydraulically entangled polyester fibers, said nonelastic webs each having a basis weight of from about 1 ounce per square yard to about 5 ounces per square yard.

18. The palindromic stretch-bonded laminate of claim 17, wherein the nonelastic web further comprises fibers selected from the group consisting of rayon fibers or wood pulp fibers.

19. The palindromic stretch-bonded laminate of claim 17, wherein said meltblown fibers are meltblown microfibers.

20. The palindromic stretch-bonded laminate of claim 17, wherein the nonelastic web is apertured.

21. A laminate which is elastic in at least one direction, said laminate comprising:

an elastic sheet comprising a polyetherester material having the following formula;

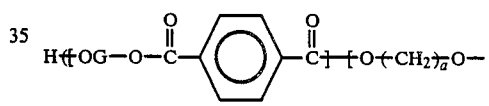

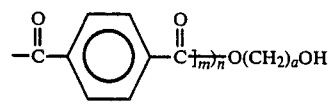

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers; and at least one nonelastic nonwoven web comprising spunlaced hydraulically entangled polyester fibers joined to said elastic sheet at least at two areas, said nonelastic web being gathered between said two areas; and wherein said spunlaced hydraulically entangled polyester nonwoven web has:

a machine direction sheet grab tensile of from about 10 pounds to 75 pounds;

a cross-machine direction sheet grab tensile of from about 5 to 50 pounds;

a machine direction trapezoid tear of from about 3 pounds to about 40 pounds;

a cross-machine trapezoid tear of from bout 2 pounds to about 45 pounds;

a thickness of from about 10 mils to about 45 mils; and a basis weight of from about 1 to 5 ounces per square yard.

22. An elastic stretch-bonded laminate adapted to stretch at least about 50 percent in at least one direction, said laminate comprising:

an elastic nonwoven web comprising fibers of a polyetherester material having the formula of;

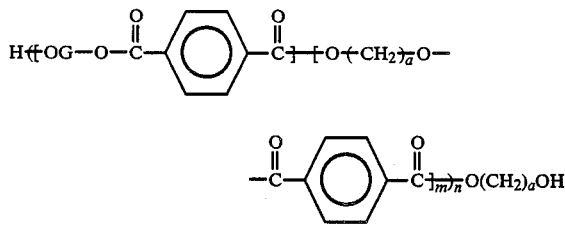

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers; and at least one nonelastic nonwoven web comprising spunlaced hydraulically entangled polyester fibers joined to said elastic web at least at two areas, said nonelastic web being gathered between said two areas wherein said spunlaced hydraulically entangled polyester nonwoven web has:

a machine direction sheet grab tensile of from about 10 pounds to 75 pounds;

a cross-machine direction sheet grab tensile of from about 5 to 50 pounds;

a machine direction trapezoid tear of from about 3 pounds to about 40 pounds;

a cross-machine trapezoid tear of from bout 2 pounds to about 45 pounds;

a thickness of from about 10 mils to about 45 mils; and a basis weight of from about 1 to 5 ounces per square yard.

23. An elastic palindromic stretch-bonded laminate adapted to stretch at least about 50 percent in at least one direction, said laminate comprising:

an inner elastic nonwoven web having a basis weight of from about 20 grams per square meter to about 100 grams per square meter, said elastic web comprising meltblown fibers of a polyetherester material having the formula of:

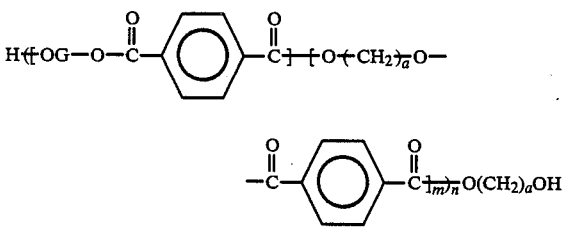

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers; and two outer nonelastic nonwoven webs comprising spunlaced hydraulically entangled polyester fibers, said nonelastic webs each having a basis weight of from about 1, ounce per square yard to about 5 ounces per square yard wherein said spunlaced hydraulically entangled polyester nonwoven web has:

a machine direction sheet grab tensile of from about 10 pounds to 75 pounds;

a cross-machine direction sheet grab tensile of from about 5 to 50 pounds;

a machine direction trapezoid tear of from about 3 pounds to about 40 pounds;

a cross-machine trapezoid tear of from bout 2 pounds to about 45 pounds;

a thickness of from about 10 mils to about 45 mils; and a basis weight of from about 1 to 5 ounces per square yard.

24. An elastic palindromic stretch-bonded laminate adapted to stretch at least about 50 percent in at least one direction, said laminate comprising:

an inner elastic nonwoven web having a basis weight of from about 20 grams per square meter to about 100 grams per square meter, said elastic web comprising meltblown fibers of a polyetherester material having the formula of:

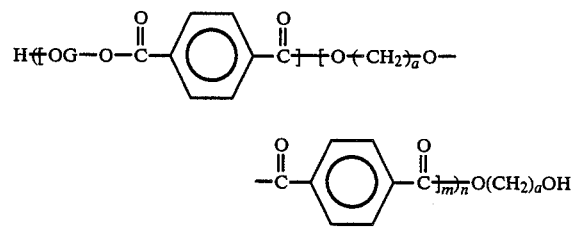

where

"G" is selected from the group including: poly(oxyethylene)-alpha,omega-diol poly(oxypropylene)-alpha,omega-diol poly(oxytetramethylene)-alpha,omega-diol and "a", "m" and "n" are positive integers;

an outer nonelastic nonwoven web comprising spunlaced hydraulically entangled polyester fibers, said spunlaced nonelastic web having:

a machine direction sheet grab tensile of from about 10 pounds to 75 pounds;

a cross-machine direction sheet grab tensile of from about 5 to 50 pounds;

a machine direction trapezoid tear of from about 3 pounds to about 40 pounds;

a cross-machine trapezoid tear of from bout 2 pounds to about 45 pounds;

a thickness of from about 10 mils to about 45 mils; and a basis weight of from about 1 to 5 ounces per square yard; and an outer nonelastic web of dry laid polyester staple fibers having a length of from about 1.0 to about 2.0 inches joined by a hot melt polyester-based, powder-form adhesive, said dry laid web having a basis weight of from about 5 grams per square meter to about 50 grams per square meter.

* * * * *

UNITED STATES PATENT AND TRADEMARK OFFICE
CERTIFICATE OF CORRECTION

PATENT NO. : 4,781,966
DATED : November 1, 1988
INVENTOR(S) : Jack D. Taylor

It is certified that error appears in the above—identified patent and that said Letters Patent is hereby corrected as shown below:

Column 2, line 65 "stetch-bonded" should read -- stretch-bonded --

Column 9, line 68 "both" should read -- Both --

Column 13, line 4 "S8010" should read -- S8001"

Signed and Sealed this

Twenty-eighth Day of March, 1989

Attest:

DONALD J. QUIGG

Attesting Officer

Commissioner of Patents and Trademarks